United States Patent [19]

Martinez

[11] 4,222,375
[45] Sep. 16, 1980

[54] IN VIVO ILLUMINATION SYSTEM UTILIZING A CANNULA WITH A CONICAL OPENING ALLOWING A SNAP-FIT WITH A CONICAL LENS AND AN APERTURE FOR FLOW OF FLUIDS AND UTILIZING A HOUSING WITH A SPHERICAL LENS FOR FOCUSING LIGHT ONTO FIBER OPTICS

[76] Inventor: Miguel Martinez, 6006 Hunt Ridge Rd., Baltimore, Md. 21210

[21] Appl. No.: 885,522

[22] Filed: Mar. 10, 1978

[51] Int. Cl.² .......................... A61B 1/06; A61B 1/12
[52] U.S. Cl. ..................................... 128/23; 128/348
[58] Field of Search ........................................ 128/4–8, 128/2 L, 23, 395, 398, 275, 276, 303.1, 348, 634–636; 350/96.16, 96.18, 96.2; 340/380; 40/546, 547; 362/32

[56] References Cited

U.S. PATENT DOCUMENTS

| | | | |
|---|---|---|---|
| 3,068,739 | 12/1962 | Hicks et al. | 128/395 X |
| 3,131,690 | 5/1964 | Innis et al. | 128/23 |
| 3,584,779 | 6/1971 | Kessler et al. | 350/96.18 X |
| 3,814,081 | 6/1974 | Mori | 128/2 L |
| 3,866,599 | 2/1975 | Johnson | 128/2 L |
| 3,902,058 | 8/1975 | Naylor et al. | 362/204 |

FOREIGN PATENT DOCUMENTS

| | | | |
|---|---|---|---|
| 2630632 | 1/1977 | Fed. Rep. of Germany | 350/96.18 |
| 2330022 | 5/1977 | France | 350/96.18 |
| 7605819 | 12/1977 | Netherlands | 350/96.18 |

OTHER PUBLICATIONS

C. P. Olinger and R. L. Ohlhaber, "Eighteen-Gauge Microscopic-Telescopic Needle Endoscope", *Surgical Neurology*, vol. 2, No. 3, May 1974, pp. 151–159.

M. Epstein, "Hypodermic Fiberscope", Conference: Application of Optical Instrumentation in Medicine, 2nd Seminar, Chicago, Nov. 1973, pp. 113–116.

*Primary Examiner*—Robert W. Michell
*Assistant Examiner*—Jeffrey W. Tayon
*Attorney, Agent, or Firm*—Robert H. Epstein

[57] ABSTRACT

An in vivo illumination system includes an elongate cannula and a fiber optic cable passing through the cannula having a lens disposed in an opening in the distal end of the cannula and a condenser lens disposed in a housing adapted to be mounted on the end of a light source such that the lenses provide concentrated light from the light source at the distal end of the cannula. The cannula has an aperture formed in a side wall thereof at the distal end to permit the flow of fluids through the cannula, and an adapter assembly is utilized to mount the condenser lens on the light source, the adapter assembly including a spherical lens for concentrating light from a lamp in the light source on the condenser lens.

10 Claims, 4 Drawing Figures

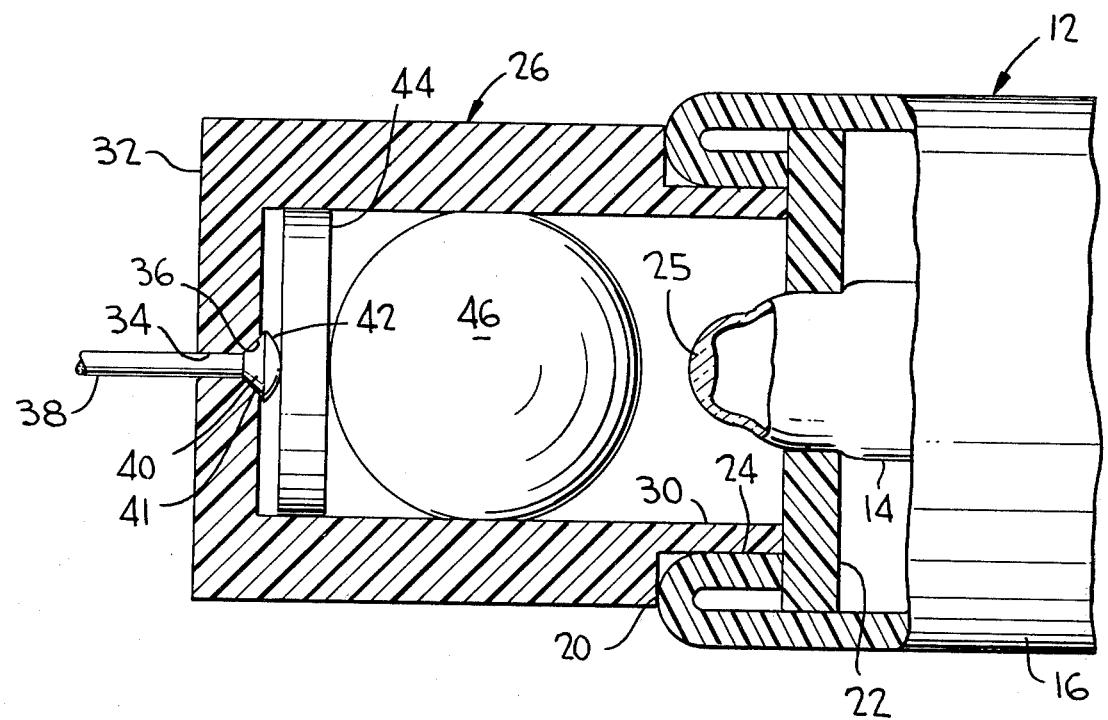

IN VIVO ILLUMINATION SYSTEM UTILIZING A CANNULA WITH A CONICAL OPENING ALLOWING A SNAP-FIT WITH A CONICAL LENS AND AN APERTURE FOR FLOW OF FLUIDS AND UTILIZING A HOUSING WITH A SPHERICAL LENS FOR FOCUSING LIGHT ONTO FIBER OPTICS

BACKGROUND OF THE INVENTION

1. Field of the Invention

The present invention pertains to illumination systems and, more particularly, to in vivo illumination systems for use during surgical operations.

2. Discussion of the Prior Art

There is a well recognized need for the precise internal or in vivo application of light during surgical operations, such need being most readily apparent in ophthalmic operations. In the past, light for such operations has been available only with complex and expensive equipment that has the disadvantages of being bulky, difficult to handle and imprecise in directing light to the desired area. The use of fiber optic systems to transmit light for such operations has been attempted; however, the structures required for such fiber optic systems have been overly expensive due to their requirement of the use of specifically designed devices for insertion in the body and light sources providing concentrated light.

SUMMARY OF THE INVENTION

Accordingly, it is a primary object of the present invention to overcome the above mentioned disadvantages of the prior art by providing an in vivo illumination system that can be utilized with a simple, inexpensive light source.

Another object of the present invention is to utilize lenses integrally formed on a fiber optic cable to concentrate light from an inexpensive light source, such as the pocket flashlight-type, and transmit the light to a surgical operating area.

The present invention has a further object in that an adapter assembly utilizes a spherical lens in the form of a plastic sphere to concentrate light from a lamp on a lens coupled with a fiber optic cable.

An additional object of the present invention is to integrally form lenses on the proximal and distal ends of a plastic fiber optic cable passing through a cannula to permit the fiber optic cable to be utilized to transmit light for use in vivo in surgical operations.

Yet another object of the present invention is to dispose a distal end of a fiber optic cable in an opening in a distal end of a cannula to permit light to be directed to a surgical operating area while fluids are simultaneously infused into or evacuated from the area via an aperture in a side wall at the distal end of the cannula.

Some of the advantages of the present invention over the prior art are that the in vivo illumination system of the present invention is inexpensive to produce utilizing commercially available components for the adapter assembly and the cannula and hub assembly and integrally formed lenses on a plastic fiber optic cable and the in vivo illumination system can be used with inexpensive light sources such as the battery-powered, pocket flashlight type.

The present invention is generally characterized in an in vivo illumination system including a light source including a casing with a lamp therein, an elongate cannula adapted for insertion in a body and having a proximal end and a distal end with an opening therein, and a fiber optic cable extending through the cannula and having a first lens formed at a distal end thereof and a second lens formed at a proximal end thereof, the first lens being disposed in the opening in the distal end of the cannula and the second lens being disposed on the light source casing to collect and concentrate light from the lamp whereby the first and second lenses provide concentrated light from the light source at the distal end of the cannula.

The present invention is further generally characterized in an adapter assembly for use with a light source having a lamp positioned at an open end of a casing including a housing adapted to be mounted on the open end of the light source casing, a condenser lens carried by the housing, and a spherical lens disposed in the housing to be positioned between the lamp and the condenser lens for gathering light from the lamp and concentrating the light on the condenser lens.

Other objects and advantages of the present invention will become apparent from the following description of the preferred embodiment taken in conjunction with the accompanying drawings.

BRIEF DESCRIPTION OF THE DRAWINGS

FIG. 2 is a broken section of the light source adapter assembly of the in vivo illumination system of FIG. 1.

DESCRIPTION OF THE PREFERRED EMBODIMENT

Figure 1:
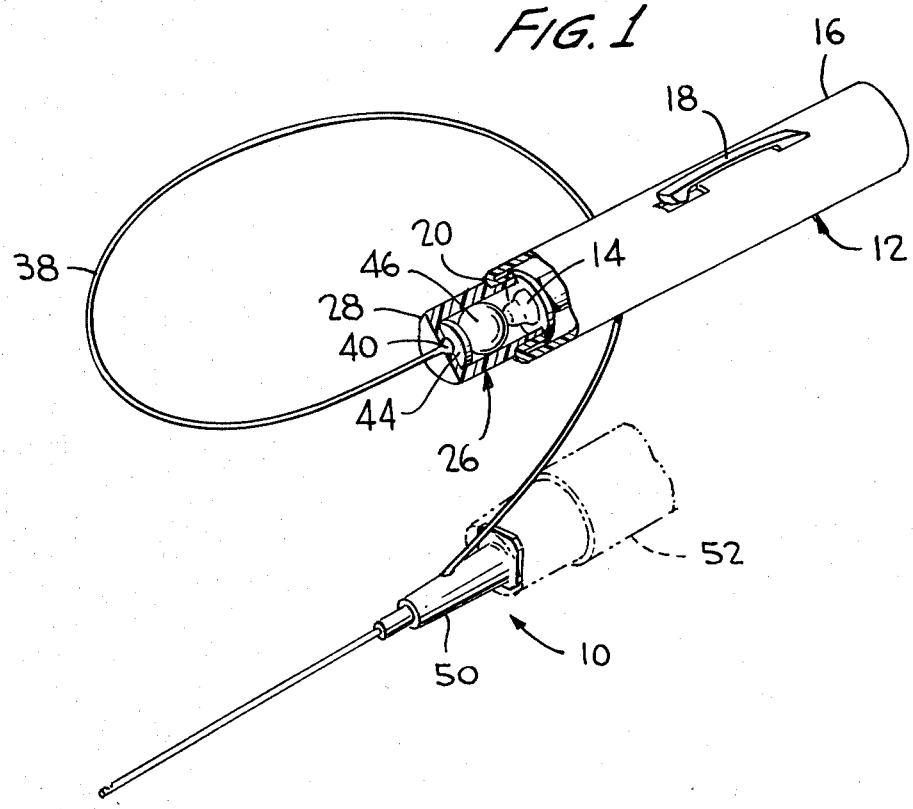
FIG. 1 is a perspective view of an in vivo illumination system according to the present invention.

An in vivo illumination system 10 according to the present invention is illustrated in FIG. 1 for use with a light source 12 having a lamp 14 powered by batteries (not shown) mounted in a plastic casing 16, the lamp being operated under the control of a switch manipulated by means of a contact arm 18 which also serves as a pocket clip. The light source 12 can be of any conventional form and construction; however, preferably, the light source is a small pocket flashlight such as that shown in U.S. Pat. No. 3,902,058 to Naylor et al. The lamp 14 is positioned at an open end 20 of the casing 16 by means of a plastic washer 22 engaging an inwardly rolled, annular flange 24 of the casing. The light emitted by lamp 14 is not well concentrated even though a biconvex lens is normally formed in the tip of the lamp envelope, as shown at 25; however, pocket flashlight light sources, such as that disclosed in U.S. Pat. No. 3,902,058, can be inexpensively produced and provide sufficient light for the purposes for which they are normally used.

In accordance with the present invention, an adapter assembly 26 is mounted on the open end 20 of the light source 12 to concentrate the light emitted by lamp 14. As best shown in FIG. 2, the adapter assembly 26 includes a cylindrical adapter housing 28 having an end 30 of reduced thickness and a diameter to be received in the open end 20 of the casing of the light source in friction fit engagement with the rolled flange 24. The housing 28 has an end wall 32 with a central bore 34 therein terminating at a conical counterbore 36 at the inner surface of the end wall 32. A plastic fiber optic cable 38, which may be formed of one or more filaments, passes through bore 34 and has an enlarged proximal end 40 formed by heating the end of the plastic fiber optic cable to form a condenser lens having a conically configured portion 41 seated in the conical counterbore 36 and a convex face 42. A circular spacer 44 made of a clear plastic material, such as vinyl, is positioned within the housing 28 abutting the convex face 42 of the lens 40, and a spherical lens 46 made of a sphere of transparent, glass-like plastic material, such as polymethylmethacrylate (Lucite) or polycarbonate (Lexan), is disposed in the housing 24 abutting the spacer 44, the spacer 44 and the sphere 46 being force fit in the housing to be held in place by friction and not requiring additional securing means. The end of lamp 14 is spaced from the spherical lens 46 by a distance equal to the thickness of spacer 44 by abutment of the end 30 of the adapter housing against washer 22.

Figure 3:
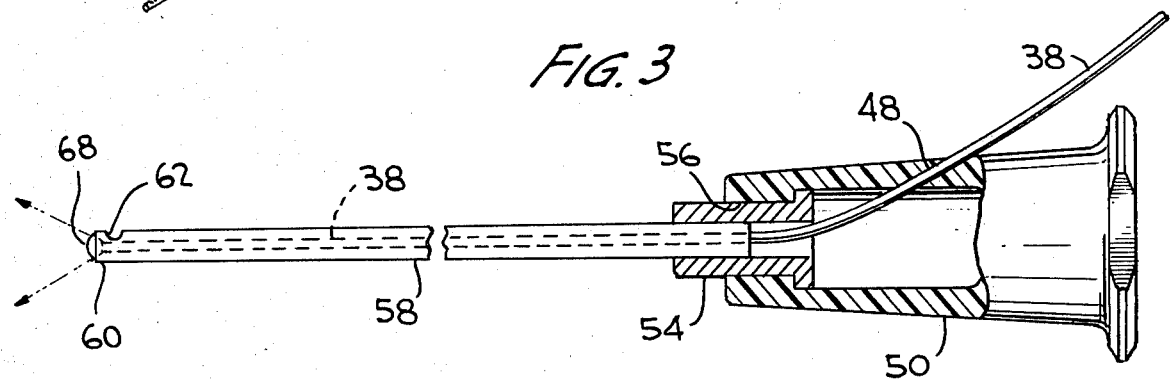
FIG. 3 is an enlarged broken view of the hub and cannula assembly of the in vivo illumination system of FIG. 1.
Figure 4:
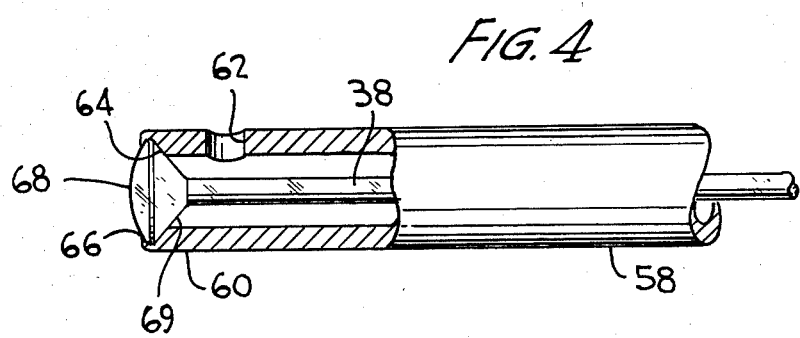
FIG. 4 is a broken section of the tip of the cannula of FIG. 3.

As best shown in FIG. 3, the fiber optic cable 38 passes through an angled bore 48 in a plastic hub 50 with a force fit to produce an hermetic seal between the fiber optic cable 38 and the hub 50 due to the characteristics of the plastic materials of which they are constructed. The hub 50 is mounted on a syringe or other source of infusion fluid 52 or a collector used with a suction source and is of conventional construction; and a metal flanged sleeve 54 is mounted in an open end 56 of the hub in sealed relation therewith. An elongate hollow metal cannula 58 is secured at its proximal end to sleeve 54 in conventional manner, and the cannular 58 has a distal end 60 with an aperture 62 in a side wall thereof and an axially aligned conical opening 64. An annular lip 66 extends radially inwardly from the opening 64 to capture a lens 68 formed at the distal end of the fiber optic cable 38 which passes through the hub 50, the sleeve 54 and the needle 58 to the distal end 60 thereof. The lens 68 is formed in the same manner as the lens 40 at the proximal end of the fiber optic cable such that a conically configured portion 69 of the lens seats in conical opening 64; and, since the fiber optic cable is made of plastic, the lens 68 can be deformed to ride over the lip 66 and snap securely into place in the opening 64, as best shown in FIG. 4.

In operation, the adapter assembly 26 is mounted on the open end 20 of the light source 12 by simply forcing end 30 into annular flange 24 with a friction fit, the spacer 44 and the spherical lens 46 being retained in position by contact with the cylindrical wall of housing 28. The source of fluid or suction 52 is coupled with the flange of hub 50 in conventional fashion, and the system is now ready for use.

The in vivo illumination system is useful in many surgical operations but is particularly adapted for use in ophthalmic surgery wherein illumination is required by the surgeon while either fluid pressure is maintained within the eye or material is evacuated from the eye. To this latter end, once the cannula is inserted in the eye, fluid can be evacuated from or infused into the eye from source 52 via hub 50 and cannula 58, the fluid flowing through aperture 62. The seating of the lens 68 in the opening 64 prevents flow of fluid through the axial opening 64. Light from lamp 14 is collected by spherical lens 46 and concentrated on condenser lens 40 at the proximal end of fiber optic cable 38 due to the spacing of the spherical lens between the lamp and the condenser lens and the optical characteristics of the spherical lens. The condenser lens 40 further acts to collect and concentrate the light such that fiber optic cable 38 transmits a great amount of the light available from lamp 14 to lens 68 at the proximal end of the cannula 58 to provide illumination in the area of the body in which the surgeon is working. In effect, the adapter assembly 26 forms a four-lens optical system composed of the biconvex lens 25 in the tip of lamp 14, the spherical lens 46 which can be considered to be two back-to-back plano-convex lenses, and the condenser lens 40 with the spherical lens centrally spaced between biconvex lamp lens 25 and condenser lens 40.

While the fiber optic cable 38 can be used with a cannula without simultaneous fluid infusion or evacuation, the illumination system 10 is particularly advantageous in that illumination and irrigation or evacuation can be accomplished with the same device requiring only a single incision. Of course, the adapter assembly 26 can be modified for use with any desired light source operating from DC batteries or normally available AC electricity; however, the pocket flashlight type light source has the advantages of being small, compact, easy to operate, inexpensive and meeting the rigourous standards for use in an operating room.

The illumination system 10 can be simple and inexpensively implemented by forming spacer 44 and spherical lens 46 from readily available components of Lucite or Lexan, forming the lenses 40 and 68 integrally with plastic fiber optic cable 38, and using a modified commercially available hypodermic needle and hub to form cannula 58 and hub 50, the hypodermic needle being cut and bored to form aperture 62 and opening 64 and the hub having angled bore 48 formed therein to provide a seal for the passage of the fiber optic cable into the hub while preventing kinking of the fiber optic cable. While the fiber optic cable 38 is preferably made of a single filament of plastic, such as Crofon made by DuPont, the fiber optic cable can be formed of one or more filaments or elements of any suitable light transmitting material. Of course, the components of the illumination system could be formed of any suitable materials. For example, the spacer 44 and the lens 46 could be formed of glass or quartz. Similarly, the illumination system can be used with any type of light source having any casing configuration, the housing 28 being provided with a suitable configuration to be mounted on the casing either with an internal or external friction fit or by means of threading or latches, such as bayonet locks.

Inasmuch as the present invention is subject to many variations, modifications and changes in detail, it is intended that all matter discussed above or shown in the accompanying drawings be interpreted as illustrative and not in a limiting sense.

What is claimed is:

1. An in vivo illumination system comprising
   a light source;
   an elongate cannula adapted for insertion in a body and having a proximal end and a distal end with an opening therein with a conical configuration; and
   a fiber optic cable made of plastic extending through said cannula and having a first lens integrally formed at a distal end thereof and a second lens integrally formed at a proximal end thereof, said first lens having a conically configured portion and being seated in said opening in said distal end of said cannula to seal said opening and said second lens being disposed adjacent said light source to collect and concentrate light whereby said first and second lenses provide concentrated light from said light source at said distal end of said cannula.

2. An in vivo illumination system as recited in claim 1 wherein said first lens has a convex face and said opening in said distal end of said cannula has a radially inwardly extending annular lip engaging said convex face of said first lens to hold said first lens in place in said opening.

3. An in vivo illumination system as recited in claim 2 wherein said opening in said distal end of said cannula is aligned with the longitudinal axis of said cannula and an aperture is positioned in a side wall of said cannula at said distal end to permit flow of fluids through said cannula.

4. An in vivo illumination system as recited in claim 2 and further comprising a plastic hub coaxially mounting said proximal end of said cannula and having a bore therethrough disposed at an angle to the axis of said cannula, said fiber optic cable extending through said bore with a force fit in sealing engagement with said hub.

5. An in vivo illumination system as recited in claim 4 wherein said light source includes a casing with a lamp therein and further comprising an adapter assembly mounting said second lens on said light source casing including a spherical lens disposed between said second lens and said lamp.

6. An in vivo illumination system as recited in claim 5 wherein said light source casing has an open end in which said lamp is positioned, said adapter assembly includes a housing engaging said open end of said casing and said spherical lens is made of plastic and is disposed in said housing with a force fit.

7. An in vivo illumination system as recited in claim 6 wherein said lamp has a biconvex lens in the tip thereof, said housing has an end wall with a bore therethrough terminating in a conical counterbore, said second lens has a conically configured portion seated in said counterbore and a convex face, and said adapter assembly includes a clear plastic spacer disposed in said housing with a force fit abutting said convex face of said second lens and said spherical lens to centrally space said spherical lens between said second lens and said biconvex lens in said lamp.

8. An in vivo illumination and infusion system for use with a light source comprising
an elongate cannula having a distal end with an opening therein for flow of fluids therethrough;
a fiber optic cable extending through said cannula and having a first end disposed at said distal end of said cannula and a second end; and
an adapter assembly for mounting said second end of said fiber optic cable on the light source including a housing disposed adjacent the lamp and a spherical lens made of plastic and disposed in said housing with a force fit, said spherical lens being centrally disposed between said second end of said fiber optic cable and the light source whereby light from said light source is concentrated on said second end of said fiber optic cable.

9. An in vivo illumination and infusion system as recited in claim 8 wherein said fiber optic cable is made of plastic and has a first lens integrally formed on said first end and a second lens integrally formed on said second end.

10. An in vivo illumination system as recited in claim 9 wherein said housing has an end wall with a bore therethrough terminating in a conical counterbore, said second lens has a conically configured portion seated in said counterbore and a convex face, and said adapter assembly includes a clear plastic spacer disposed in said housing with a force fit abutting said convex face of said second lens and said spherical lens.

* * * * *